(12) United States Patent
Fujii et al.

(10) Patent No.: US 7,428,771 B2
(45) Date of Patent: Sep. 30, 2008

(54) CLIP FOR DIVIDING TWO LIQUIDS

(75) Inventors: Junya Fujii, Hiroshima (JP); Hideyasu Miyahara, Hiroshima (JP); Seishin Tanaka, Hiroshima (JP)

(73) Assignee: JMS Co., Ltd., Hiroshima-shi (JP)

( * ) Notice: Subject to any disclaimer, the term of this patent is extended or adjusted under 35 U.S.C. 154(b) by 0 days.

(21) Appl. No.: 10/531,999

(22) PCT Filed: Oct. 23, 2002

(86) PCT No.: PCT/JP02/10980

§ 371 (c)(1),
(2), (4) Date: Oct. 25, 2005

(87) PCT Pub. No.: WO2004/037158

PCT Pub. Date: May 6, 2004

(65) Prior Publication Data

US 2006/0107502 A1    May 25, 2006

(51) Int. Cl.
*B65D 33/16* (2006.01)
*B65D 77/10* (2006.01)

(52) U.S. Cl. ...................... 24/543; 24/30.5 R
(58) Field of Classification Search ............... 24/543, 24/30.5 R, 517, 518; 606/120
See application file for complete search history.

(56) References Cited

U.S. PATENT DOCUMENTS

| | | | | |
|---|---|---|---|---|
| 2,271,133 A | * | 1/1942 | Thoresen | 24/170 |
| 3,171,184 A | * | 3/1965 | Posse | 606/120 |
| 4,212,303 A | * | 7/1980 | Nolan | 606/120 |
| 4,834,096 A | * | 5/1989 | Oh et al. | 606/158 |
| 5,050,272 A | * | 9/1991 | Robinson et al. | 24/30.5 R |
| 5,079,806 A | * | 1/1992 | Allen | 24/30.5 R |
| 5,123,146 A | | 6/1992 | Olson | |
| 5,125,133 A | * | 6/1992 | Morrison | 24/30.5 R |
| 5,598,608 A | * | 2/1997 | Naslund | 24/30.5 R |
| 5,604,959 A | * | 2/1997 | Bowen | 24/30.5 R |
| 6,058,572 A | * | 5/2000 | Folkmar | 24/30.5 R |
| 7,131,169 B2 | * | 11/2006 | Folkmar | 24/30.5 R |
| 2004/0250385 A1 | * | 12/2004 | Folkmar | 24/543 |

(Continued)

FOREIGN PATENT DOCUMENTS

EP    1 440 896 A1    7/2004

(Continued)

*Primary Examiner*—Robert J Sandy
(74) *Attorney, Agent, or Firm*—Westerman, Hattori, Daniels & Adrian, LLP.

(57) ABSTRACT

A clip which solves a technical problem that the latching of the clip is not easily released by the external force caused by falling, etc., and is easily released when the clip is used. The clip has opposed clipping arms capable of forming an independent and separate space by pressing and holding a clipped object constituted of a flexible hollow member between them. The clip has a latching means on one end of the opposed clipping arm, which has a latching part capable of latching the clipping arms. The clip further has a latching releasing means capable of releasing the latching by an external force headed to an external direction from the clipping arm. The latching means has a supporting point part acting the latching releasing force, added to the latching means by the latching releasing means, to the direction to release the latching of the latching part.

9 Claims, 2 Drawing Sheets

U.S. PATENT DOCUMENTS

2005/0120521 A1 * 6/2005 Folkmar .................. 24/30.5 R

FOREIGN PATENT DOCUMENTS

| JP | 02-060580 B2 | | 12/1990 |
| JP | 05-008998 Y2 | | 3/1993 |
| JP | 10-5313 | | 1/1998 |
| JP | 2000-229648 | * | 8/2000 |
| JP | 2002-321746 | * | 11/2002 |

* cited by examiner

CLIP FOR DIVIDING TWO LIQUIDS

TECHNICAL FIELD

The present invention relates to a clip for dividing two liquids (hereinafter also referred to as clip, simply) used for blocking a tube, or for blocking or dividing into multiple compartments an opening of a flexible hollow member such as a bag-like article.

As for said bag-like article, a bag for medical or pharmaceutical use such as an infusion solution bag and the like can be exemplified, but it is not limited for medical or pharmaceutical use, and it can be used in fields where it is necessary to block a flexible hollow member or form an independent space therein with the clip.

BACKGROUND ART

There is a clip that is used for subdividing solution chambers in bags for medical or pharmaceutical use that are used as infusion solution bags or dialysate bags and the like, disclosed in Utility Model Publication No. 5-8998. This clip has a construction wherein catching parts fixing each other are provided to each of both end parts of two clip pieces formed separately, and a linear holding part that clips both sides of the infusion solution bag in the central longitudinal direction excluding the prescribed area at both ends of each clip piece, is formed.

Moreover, there is a clamp that clips a tube or a bag to seal the inner space of the clipped object in a liquid tight condition, disclosed in Japanese Patent Publication No. 4-193179. It is composed of the following: a catching means located at an end of the clamp, binding two plate-like members in a detachable way; a clipping part composed of two plate-like members having pressing projecting parts being parallel to each other, in the longitudinal direction of its inner surface; a detachable latching means maintaining said clipping part in a condition that the clipped object is clipped; and a grasping part located at the other end of the clamp, to give a force to said clipping part for clipping said clipped object by grasping with the finger and the like.

There is a clamp that clips a tube or a bag to seal the inner space of the clipped object in a liquid tight condition, disclosed in Japanese Laid-Open Patent Application No. 2000-229648. This is a clip that clips the prescribed part of the clipped object from both sides, binding a pair of pinching levers by the axis in a detachable and oscillating way at one end of the clip. The other end part of both pinching levers is composed so that it is able to fix and latch by a latching means. An insertion channel is formed along the longitudinal direction of the pinching lever in the facing surface from the second pinching lever to the first pinching lever. An insertion line section, which is abutting to the side wall part by being inserted to this insertion channel, is projectingly formed to the facing surface from the first pinching lever to the second pinching lever. It has a construction that a film material to be clipped is pressure-bonded between the insertion channel of the second pinching lever and the insertion line section of the first pinching lever inserted into the insertion channel. As for the clamp sealing the opening of the bag and the like, there is one disclosed in Japanese Patent Publication No. 2-60580. As for the clip comprising a clipping means wherein two rims are facing each other by the hinge binding, and a locking element provided at a free end of the rim, the rim comprises a leg being able to press resiliently to the side facing to the rim; and rim 2 provides a channel having a wide opening that can accept said leg together with the object to be clipped, and a taper inner wall surface that leads leg 3 to the narrow back part.

As described above, as for clips for clipping an object to be clipped, such as a tube or a flexible hollow member, for example, a bag-like article, various kinds of clips are publicly announced.

As for the aforementioned clip, in particular, the clip for a bag-like article, for example, a plastic bag, there are two types of clips: one is clips that have the latching means and the part to be pressed integrally (hereinafter referred to as type A), the other is clips that have the latching means in a place different from the part to be pressed (hereinafter referred to as type B). Type A excels in an airtight function, but it has a problem with easiness of production and opening. On the other hand, type B excels in easiness of production, opening and handling, but it has a difficulty in ensuring an airtight function.

In case of clips of type B, as the latching means have to be reinforced to ensure the airtight function when the clips are elongated to the longitudinal direction, the handling will worsen, for example, significant force will be required to open and close the clips. When trying to improve the handling, the clips will come off too easily by the impact caused by falling, etc., added to a part to be handled. In other words, there is a problem in the clips of type B that a contradictory technical problem, which is, "a clip difficult to come off by the impact caused by falling, etc., and easy to be removed by users when used", has to be solved. It has been difficult for the person skilled in the art to solve this problem.

An object of the present invention is to provide a clip for dividing two liquids that solves the aforementioned problem.

DISCLOSURE OF THE INVENTION

In case of conventional clips wherein an external force from an external direction is added to a clipping arm when releasing the latching of clips, the direction of the force (hereinafter also referred to as latching releasing force) is the same as that of an external impactive force such as falling, therefore, the latching of clips is released when falling, etc. The present inventors have solved this problem by finding that a clip that solves the aforementioned problem, which is, "a clip difficult to come off by the impact caused by falling, etc., and easy to be removed by users when used", can be provided by making a structure of the latching means of the clips capable of releasing the latching by adding an external force the latching arm to the external direction (therefore, by adding an external force from the external direction to the clipping arm, the clips are closed), and that as such structure, a structure that has a supporting point part acting the latching releasing force added to the latching means to the direction to release the latching of the latching part can be used. The present inventors have thus reached the present invention.

The present invention comprises a clip comprising opposed clipping arms capable of forming an independent and separate space by pressing and holding therebetween a clipped object constituted of a flexible hollow member, and a latching means, disposed on one end of the opposed clipping arm, which has a latching part capable of latching the clipping arms which are pressing and holding the clipped object between the opposed clipping arms, wherein the clip has a latching releasing means capable of releasing the latching by an external force headed to an external direction from the clipping arm (hereinafter also referred to as latching releasing force), and a structure of the latching means has a supporting point part acting the latching releasing force, added to the latching means by the latching releasing means, to the direction to release the latching of the latching part.

The latching means is disposed at one or both ends of the clipping arm, and an example of the external force headed to the external direction from the clipping arm includes a force headed to the direction of the arrow shown in FIG. 1.

In addition, the present inventors have found that in order to solve the aforementioned technical problem, it is further effective to dispose the latching part of the latching means at the latching releasing means side of the supporting point part in the clip mentioned above. In other words, the present invention comprises a clip wherein the latching part of the latching means is disposed at the latching releasing means side of the supporting point part. By adopting this structure, the latching means can be released very easily also by the latching releasing force headed to the external direction from the clipping arm, and the latching is maintained more safely against the force headed from the external direction to the direction of the clipping arm, such as external impactive force.

Further, the present inventors have found that in order to solve the aforementioned technical problem, the clip wherein the latching part of the latching means is constituted of a male member and a female member, and one of the male member and the female member is formed on a tip end of an elastic piece capable of oscillating with the use of the supporting point part as a fulcrum, by the latching releasing means (formed on one tip end of the clipping arm), and the other of the male member and the female member is formed on the other tip end of the clipping arm, in each clip mentioned above, is effective. In other words, the clip of the present invention comprises the clip wherein the latching means is constituted of the latching part having a male member and a female member, and of an elastic piece formed on one tip end of the clipping arm and capable of oscillating with the use of the supporting point part as a fulcrum by the latching releasing means; one of the male member and the female member is formed on a tip end of the elastic piece; and the other of the male member and the female member is formed on the other tip end of the clipping arm, in each clip mentioned above. This clip is capable of releasing the latching of the latching part by oscillating the elastic piece with the use of the supporting point part as a fulcrum by the latching releasing means.

As for the clip of the present invention, a clip wherein the latching releasing means and the latching means, or the latching releasing means, the latching means and the clipping arm are integrally molded is preferable.

Examples of the latching releasing means include those comprised of a band shape elastic piece whose tip end is bound to the elastic piece of the latching means, those comprised of a pull-tab integrally molded with the band shape elastic piece bound to the elastic piece of the latching means, or those comprised of the band shape elastic piece bound to the elastic piece of the latching means and a thread-like article bound to the band shape elastic piece.

The clip of the present invention has is a structure wherein the other end of the clipping arm on which the latching means is formed is bound by an axis in an oscillating way, or by a hinge integrally molded with the clipping arm and formed on the other end, opposite the side the latching means is formed, in an oscillating way.

BEST MODE OF CARRYING OUT THE INVENTION

The Clipping Arm

There is no particular limitation to types of synthetic resins constituting the opposed clipping arms, 5, 10 shown in FIGS. 1 and 2, which constitute the clip of the present invention, however, for the balance between the characteristics of the hinge required by the clip of the present invention, and the rigidity required to ensure the airtight condition of the tube or the flexible hollow member, it is preferable to be made with polyoxymethylene resin (hereinafter referred to as POM), polypropylene resin (hereinafter referred to as PP resin), polycarbonate resin (hereinafter referred to as PC resin), or to be made by mixing reinforcer such as glass fiber (hereinafter referred to as GF), carbon fiber (hereinafter referred to as CF) and the like to said resin.

Examples of combination of these resins and reinforcers include, GF- or CF-containing POM (hereinafter referred to as POM+GF or POM+CF), GF- or CF-containing PP (hereinafter referred to as PP+GF or PP+CF) or GF- or CF-containing PC (hereinafter referred to as PC+GF or PC+CF), however, from the viewpoint of the aforementioned balance between the characteristics of the hinge and the rigidity required to ensure the airtight condition of the tube or the flexible hollow member, POM+GF is particularly preferable.

Figure 2:
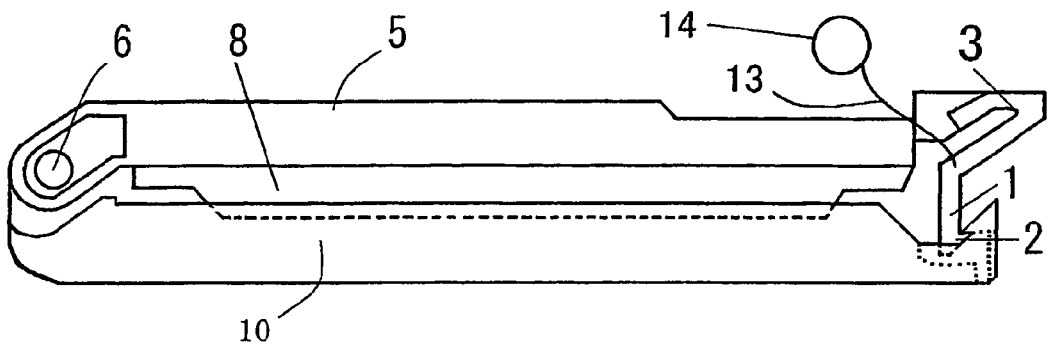
FIG. 2 describes the constitution of the clipping arm, the latching means and the latching releasing means in another aspect (a thread-like article as a latching releasing means) of the clip of the present invention.
Figure 3:
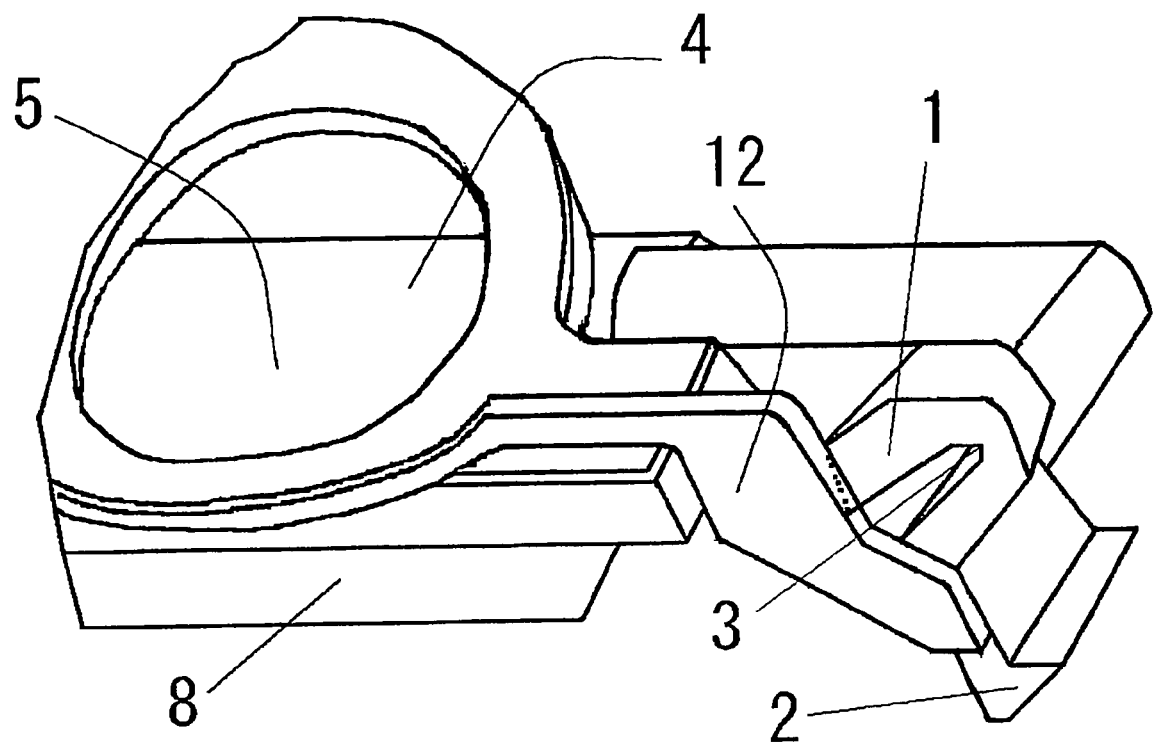
FIG. 3 is an enlarged view showing the vicinity of the latching means and the latching releasing means of the clip of the present invention.

The opposed clipping arms 5, 10 may have a structure wherein they are bound to a free end without a latching means by axis (6, 7) in an oscillating way as shown in FIG. 2, or as another aspect, like the first invention, a structure wherein they are bound by a hinge integrally molded with the clipping arms and formed on a free end without a latching means, in an oscillating way (not shown), or a structure wherein a means for binding by axis (6, 7), or for binding the clipping arms such as a hinge is not particularly disposed, and each of the clipping arms 5, 10 has on its both ends the latching means, which is one of major characteristics of the present invention as mentioned above, enabling each of the clipping arms 5, 10 to latch each other.

The clipping arms 5, 10 may have a structure having an insertion channel 9 into which an insertion ridge section 8 mentioned below can be inserted along the longitudinal direction of the clipping arm in the facing surface from one opposed clipping arm 10 to the other clipping arm 5, or a structure having the insertion ridge section 8 to be inserted into the insertion channel 9 in the facing surface from the other clipping arm 5 mentioned above to one opposed clipping arm 10 mentioned above. As the structure thus described, known techniques described in the section of Background Art, for instance, the structure described in Japanese Patent Publication No. 2-60580, is exemplified.

The Latching Means

The latching means is constituted of, at least, a latching part and a supporting point part acting the latching releasing force, added by the latching releasing means mentioned below, to the direction to release the latching of the latching part, and has a structure capable of releasing the latching of the latching means by the latching releasing means mentioned below.

Figure 1:
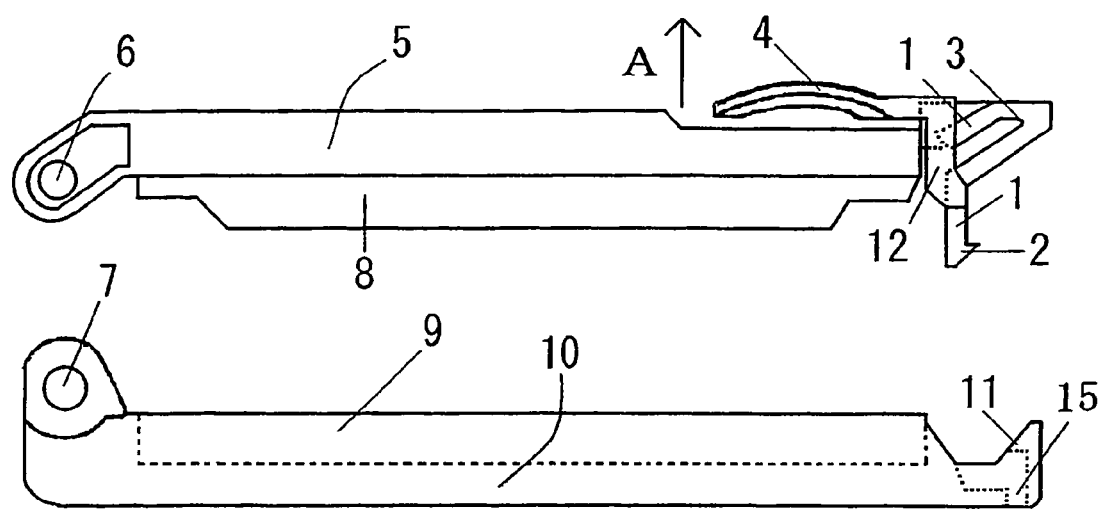
FIG. 1 describes the constitution of the clipping arm, the latching means and the latching releasing means of the clip of the present invention.

An example of the latching means includes, as shown in FIGS. 1 and 2, the latching means having a structure wherein;

(1) the latching part is comprised of a male member 2, a female member 11 formed from a projection part capable of latching the male member 2, and a through hole 15,
(2) there is an elastic piece 1 which can oscillate by a latching releasing means comprised of a band shape elastic piece 12 and a pull-tab 4, and forms a supporting point part 3 acting a latching releasing force, added by the latching releasing means, to the direction to release the latching of the hook-like male member 2 and the female member 11 of the latching part,
(3) the hook-like male member 2 is formed at the tip end of the elastic piece 1, and the through hole 15 and the female member 11 of a projection part 11 are formed on one tip end of the other clipping arm 10, and
(4) the latching part formed from the hook-like male member 2, the female member 11 and the through hole 15 is disposed at the latching releasing means side of the supporting point part 3.

A concave shape such as a recess can be used instead of the through hole 15.

Further, this latching means can make the clip of the present invention clip an object to be clipped by adding an external force to the opposite side of A shown in FIG. 1, in other words, inside the clipping arms 5, 10.

In addition, it is preferable that the latching means is integrally molded with the clipping arm, and that the resins suitable to form the clipping arm mentioned above are adopted as a resin to form the latching means and the clipping arm.

The Latching Releasing Means

The latching releasing means binds to the latching means, transmits a latching releasing force to the latching means, and via the supporting point part 3, fulfills its function to release the latching of the hook-like male member 2 and the female member 11 of the latching part.

Further, as for a material to constitute the latching releasing means, a material hard to transmit an external impactive force to the latching part is preferable. A flexible material is preferable because a material which transmits easily a force caused by a releasing operation to the latching part is preferable.

As a constitution of the latching releasing means, for example, the followings are exemplified:
(1) those constituted of a flexible band shape elastic piece 12, made of a synthetic resin, bound to the elastic piece 1 of the latching means,
(2) those constituted by binding the pull-tab 4 to the band shape elastic piece 12 bound to the elastic piece 1 of the latching means (FIG. 1),
(3) those constituted of a thread-like article 13 or a thread-like article bound to the elastic piece 12 of the latching means (FIG. 2).

The latching of the hook-like male member 2 and the female member 11 can be released when users add a force to the latching releasing means to the direction A shown in FIG. 1, in other words, the direction toward the outside of the clipping arms 5, 10, and on the contrary, when the clip falls, the latching is safe because it is not released by an external impactive force the clip receives, headed to the direction A shown in FIG. 1, in other words, the direction toward the inside of the clipping arms 5, 10.

The clip shown in FIG. 1 uses a pull-tab as a latching releasing means, and the clip shown in FIG. 2 uses a thread-like article as a latching means. With the use of the pull-tab and the thread-like article, the latching of the clip can be released with less force, and the latching becomes safer for the external impactive force headed to the direction toward the inside of the clipping arms 5, 10.

It is preferable in view of production that the clipping arm, the latching means of the clipping arm, and the latching releasing means for releasing the latching means are integrally molded in the clip of the present invention except when the thread-like article is used as the latching releasing means, however, a clip which is not integrally molded can be also used.

In addition, the thread-like article 13 or loops made of the thread-like article such as "rubber band", used as a member which constitutes the latching releasing means or a member for the latching releasing means in the clip of the present invention, can exert outstanding effect in the point that it is hard to transmit an external impactive force to a latching part.

Further, as shown in FIG. 2, a ring 14, which looks like a pull-tab, may be bound to the thread-like article 13 on the side to which the latching releasing force is added.

INDUSTRIAL APPLICABILITY

As described above, the clip of the present invention is useful as a clip in the fields wherein it is necessary to block a flexible hollow member, for example, bags for medical or pharmaceutical use such as infusion solution bags, and to form an independent space therein. The clip exerts an outstanding effect as follows; the clipping can be maintained when an external impact force such as those caused by falling is added, therefore, it is safe, while users can release the latching of the clip with less force when using the clip.

The invention claimed is:
1. A clip, comprising:
a first clipping arm and a second clipping arm capable of pressing and holding therebetween a clipped object constituted of a flexible hollow member, thereby forming an independent, separate space in the clipped object,
a latching portion having a male member and a female member to engage with the male member, and
a latching releaser to release engagement between the male member and the female member, wherein
(1) either the first clipping arm or the second clipping arm has an elastic member at a second end of the clip,
(2) the latching releaser is connected to the elastic member at a connecting point and extending toward a first end of the clip and along an outer side of the first or second clipping arm,
(3) either the male member or the female member is disposed on a tip end of the elastic member, the other of the male member or the female member being disposed on the other of first clipping arm and the second clipping arm, and
(4) the elastic member has a fulcrum disposed further from the first end of the clip than the connecting point.

2. The clip according to claim 1, wherein the latching releaser and the latching portion are integrally molded.

3. The clip according to claim 2, wherein the latching releaser, the latching portion and the first and the second clipping arms are integrally molded.

4. The clip according to claim 1, wherein the latching releaser is a band shaped elastic piece whose tip end is bound to the elastic member of the latching portion.

5. The clip according to claim 4, wherein the latching releaser is comprised of a pull-tab integrally molded with the band shaped elastic piece bound to the elastic member of the latching means.

6. The clip according to claim 1, wherein the latching releaser is comprised of a thread-like article or a thread-like article bound to an elastic piece of the latching portion.

7. The clip according to claim 1, wherein the first clipping arm and the second clipping arm are pivotally connected at the first end of the clip.

8. The clip according to claim 1, wherein the first clipping arm and the second clipping arm are pivotally connected by a hinge portion integrally molded with at least one of the first clipping arm or the second clipping arm at the first end of the clip.

9. The clip according to claim 1, wherein at least the first clipping arm and the second clipping arm are comprised of a resin made by mixing a glass fiber into a polyoxymethylene resin.

* * * * *